United States Patent
Mimura et al.

(10) Patent No.: US 8,045,153 B2
(45) Date of Patent: Oct. 25, 2011

(54) SPECTRAL IMAGE PROCESSING METHOD, SPECTRAL IMAGE PROCESSING PROGRAM, AND SPECTRAL IMAGING SYSTEM

(75) Inventors: Masafumi Mimura, Ageo (JP); Hisashi Okugawa, Yokosuka (JP)

(73) Assignee: Nikon Corporation, Tokyo (JP)

( * ) Notice: Subject to any disclaimer, the term of this patent is extended or adjusted under 35 U.S.C. 154(b) by 564 days.

(21) Appl. No.: 11/913,294

(22) PCT Filed: Feb. 1, 2007

(86) PCT No.: PCT/JP2007/051699
§ 371 (c)(1),
(2), (4) Date: Oct. 31, 2007

(87) PCT Pub. No.: WO2007/097171
PCT Pub. Date: Aug. 30, 2007

(65) Prior Publication Data
US 2009/0128806 A1    May 21, 2009

(30) Foreign Application Priority Data
Feb. 23, 2006    (JP) .................. 2006-046509

(51) Int. Cl.
*G01J 3/30*     (2006.01)
*G06K 9/00*    (2006.01)
*G01N 33/48*  (2006.01)

(52) U.S. Cl. .......... 356/317; 356/318; 382/167; 702/22; 702/27

(58) Field of Classification Search .......... 356/317–318, 356/417, 326, 328; 382/128, 133, 190, 276, 382/235, 243, 277; 702/27, 22, 30
See application file for complete search history.

(56) References Cited

U.S. PATENT DOCUMENTS

| 5,798,262 | A   | 8/1998 | Garini et al. |
| 5,991,456 | A   | 11/1999 | Rahman et al. |
| 6,015,667 | A   | 1/2000 | Sharaf |
| 6,341,257 | B1* | 1/2002 | Haaland .................. 702/27 |
| 6,415,233 | B1* | 7/2002 | Haaland .................. 702/22 |
| 6,750,964 | B2* | 6/2004 | Levenson et al. ......... 356/326 |
| 6,763,308 | B2* | 7/2004 | Chu et al. ................ 702/19 |

(Continued)

FOREIGN PATENT DOCUMENTS

JP    11-185036 A    7/1999

(Continued)

OTHER PUBLICATIONS

Timo Zimmermann et al., "Spectral imaging and its applications in live cell microscopy", FEBS Letters 546 (2003), p. 87-92, May 16, 2003.

(Continued)

Primary Examiner — Sang Nguyen
(74) Attorney, Agent, or Firm — Miles & Stockbridge P.C.

(57) ABSTRACT

A spectral image processing system and method of performing robust unmixing on measurement noise. Based on an observed spectral image acquired from a specimen and emission spectral data of each of plural materials contained in the specimen, a contribution of each of the plural materials to the observed spectral image is unmixed by a process, including an evaluating step of evaluating reliability of each component of the observed spectral image based on a predicted spectral image of the observed spectral image, and a reflecting step of reflecting a result of the evaluation in a content of the unmixing.

14 Claims, 7 Drawing Sheets

U.S. PATENT DOCUMENTS

| | | | |
|---|---|---|---|
| 6,888,963 B2* | 5/2005 | Nichogi | 382/167 |
| 6,894,699 B2 | 5/2005 | Someya et al. | |
| 6,906,859 B2* | 6/2005 | Nihoshi et al. | 359/389 |
| 7,129,959 B2 | 10/2006 | Someya et al. | |
| 7,283,684 B1* | 10/2007 | Keenan | 382/276 |
| 7,321,791 B2* | 1/2008 | Levenson et al. | 600/476 |
| 7,420,674 B2* | 9/2008 | Gerstner et al. | 356/318 |
| 7,471,831 B2* | 12/2008 | Bearman et al. | 382/191 |
| 7,555,155 B2* | 6/2009 | Levenson et al. | 382/133 |
| 2002/0047907 A1 | 4/2002 | Chen et al. | |
| 2002/0090630 A1 | 7/2002 | Hazama | |
| 2005/0111017 A1* | 5/2005 | Takahashi et al. | 358/1.9 |
| 2006/0108540 A1 | 5/2006 | Nakajima | |
| 2006/0119896 A1 | 6/2006 | Chen et al. | |
| 2007/0088535 A1* | 4/2007 | Ten | 703/21 |
| 2007/0099535 A1 | 5/2007 | Riebersal et al. | |
| 2009/0080722 A1* | 3/2009 | Okugawa et al. | 382/128 |

FOREIGN PATENT DOCUMENTS

| | | |
|---|---|---|
| JP | 2000-503774 A | 3/2000 |
| JP | 2000-511315 A | 9/2000 |
| JP | 2002-44570 A | 2/2002 |
| JP | 2002-152762 A | 5/2002 |
| JP | 2002-168868 A | 6/2002 |
| JP | 3351536 B2 | 9/2002 |
| JP | 2003-083894 A | 3/2003 |
| JP | 2004-163312 A | 6/2004 |
| WO | WO 2005/013622 A1 | 2/2005 |
| WO | WO 2005/036143 A1 | 4/2005 |

OTHER PUBLICATIONS

Dickinson et al., "Multi-Spectral Imaging and Linear Unmixing Add a Whole New Dimension to Laser Scanning Fluorescence Microscopy", Bio Techniques, vol. 31, No. 6, 2001, pp. 1272, 1274-1276, 1278.

* cited by examiner

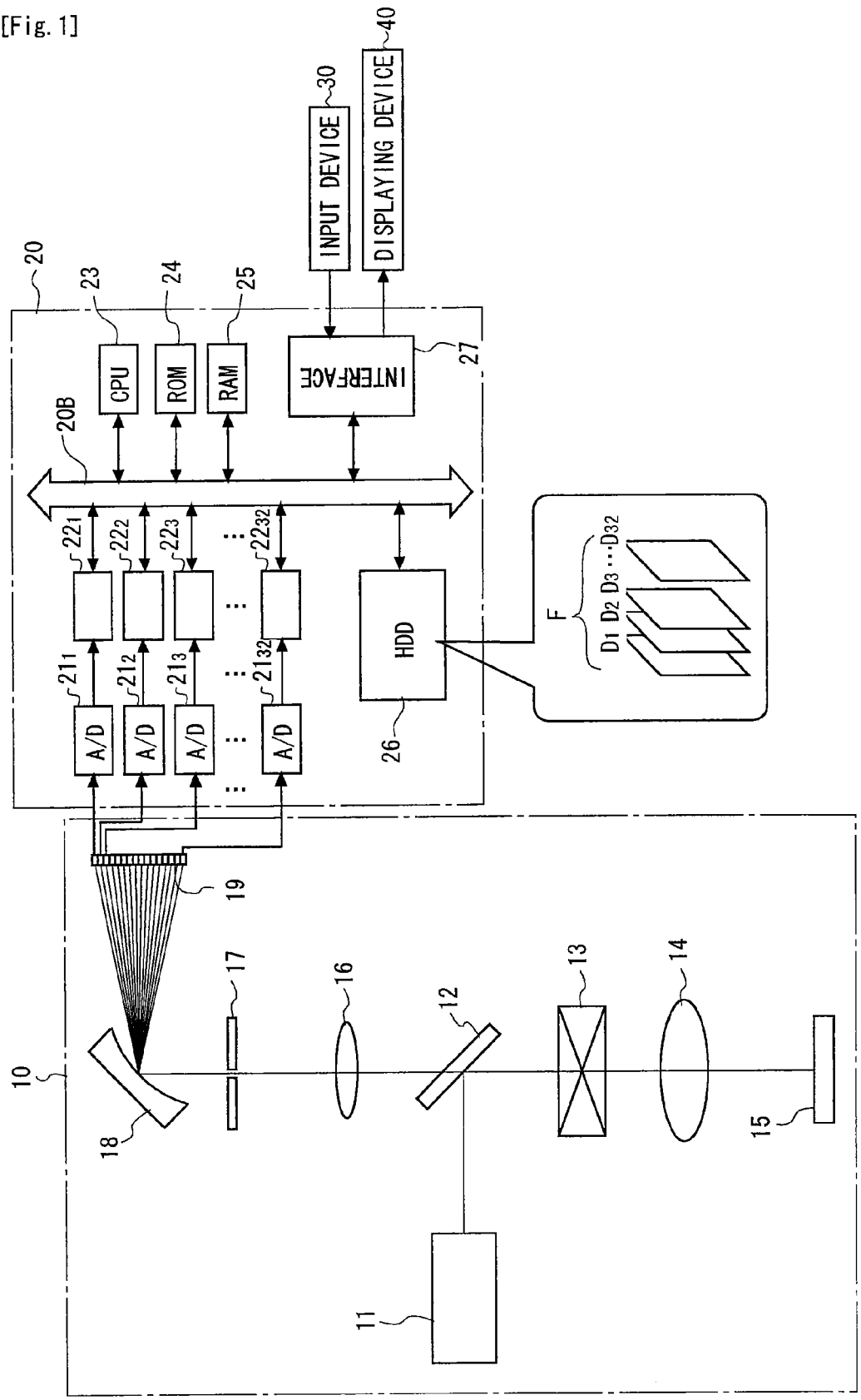

[Fig. 2]
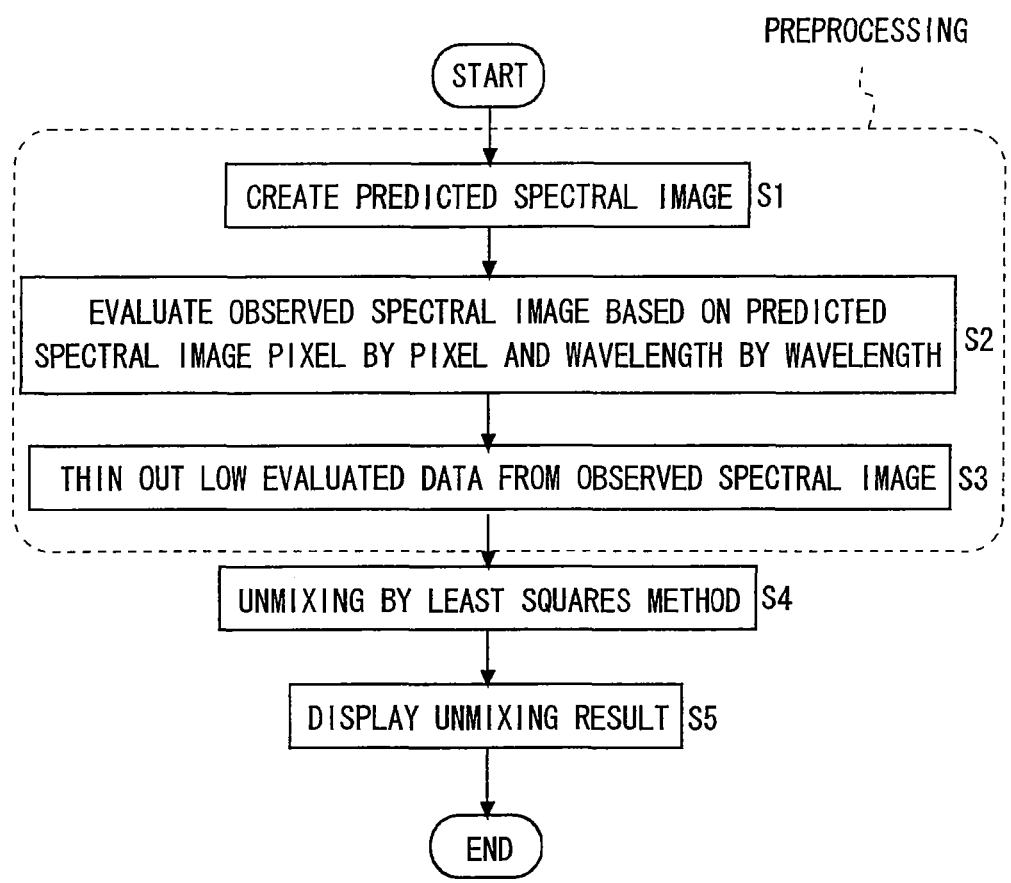

[Fig. 3]
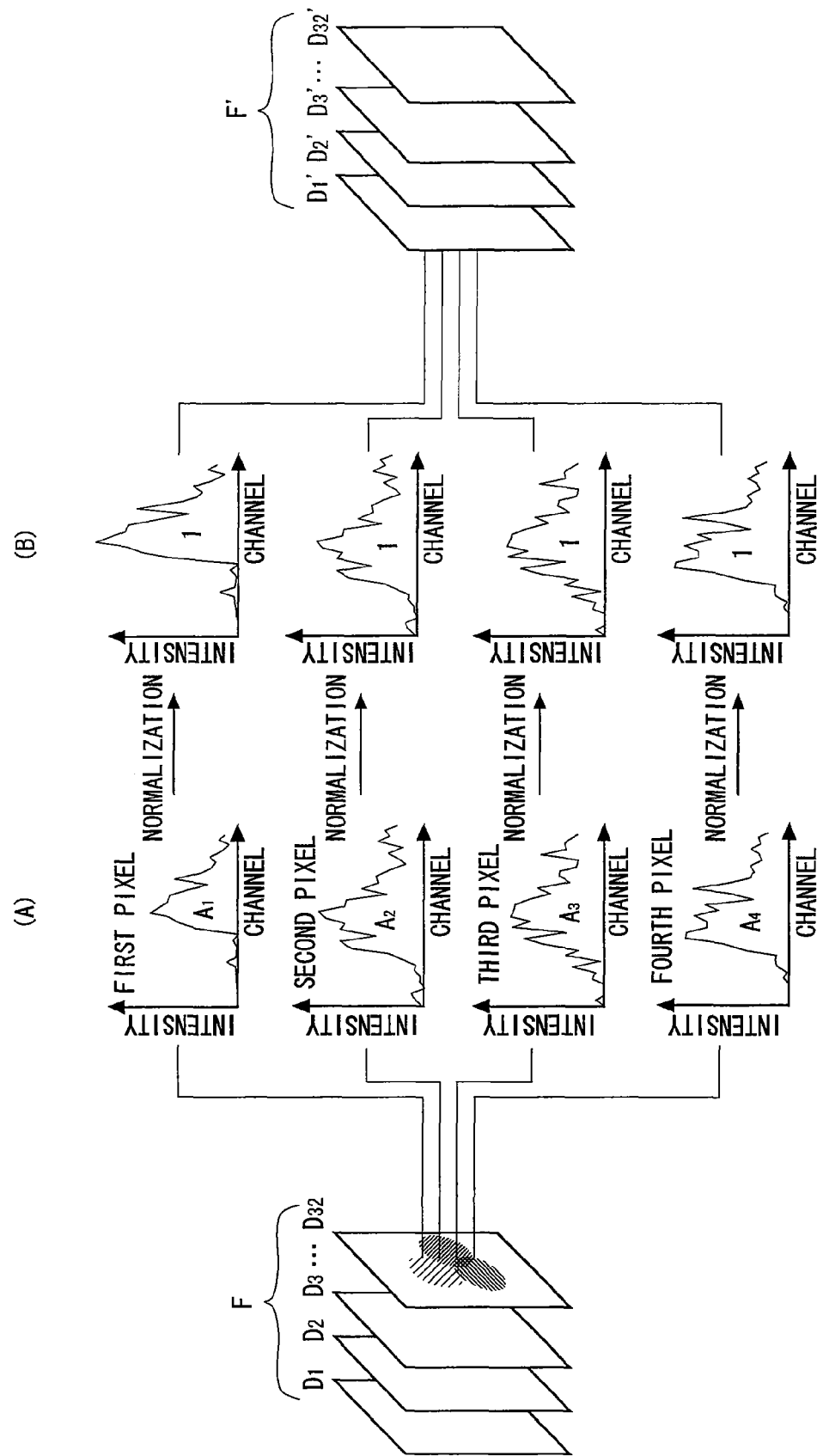

[Fig. 4]
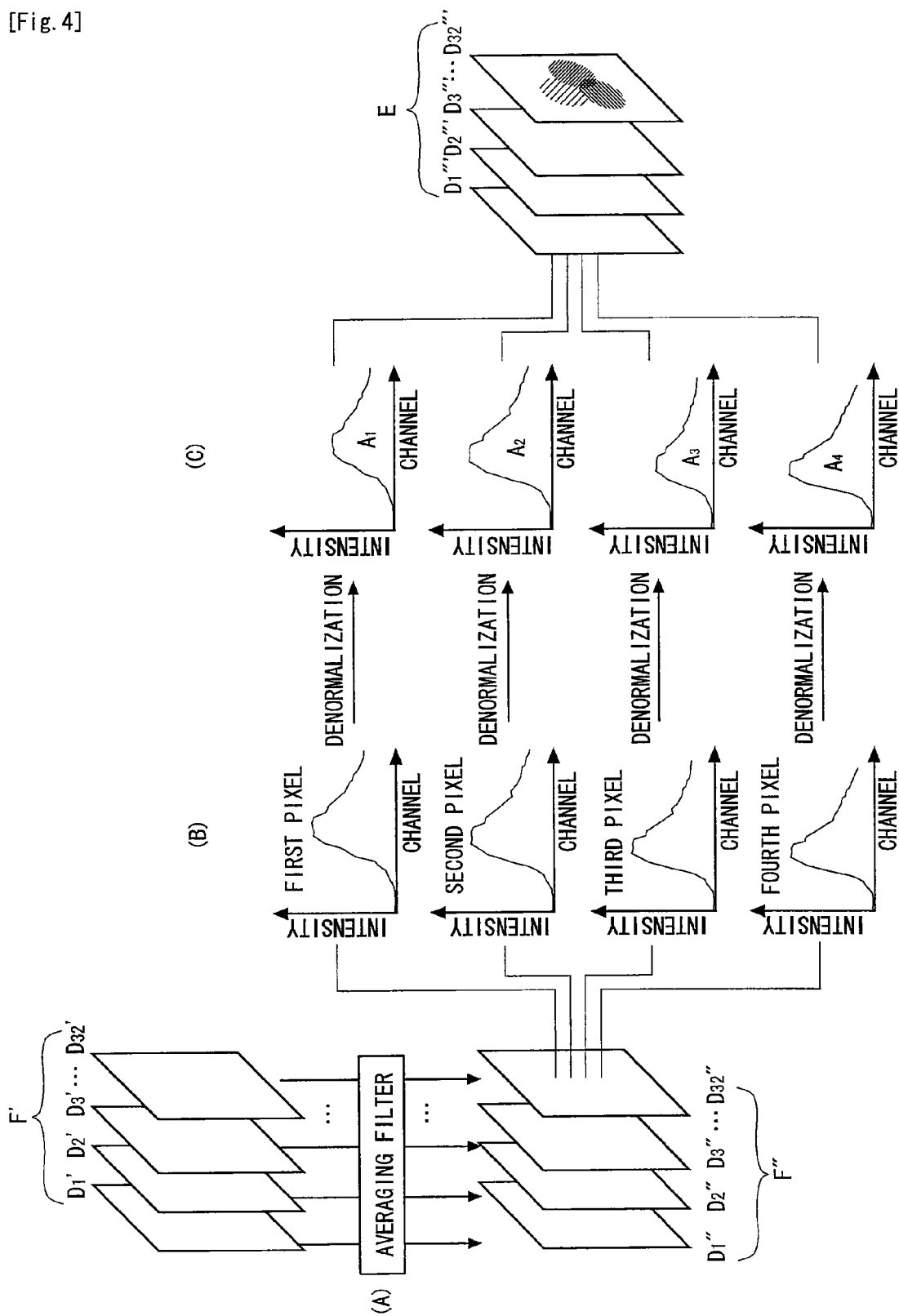

[Fig. 5]
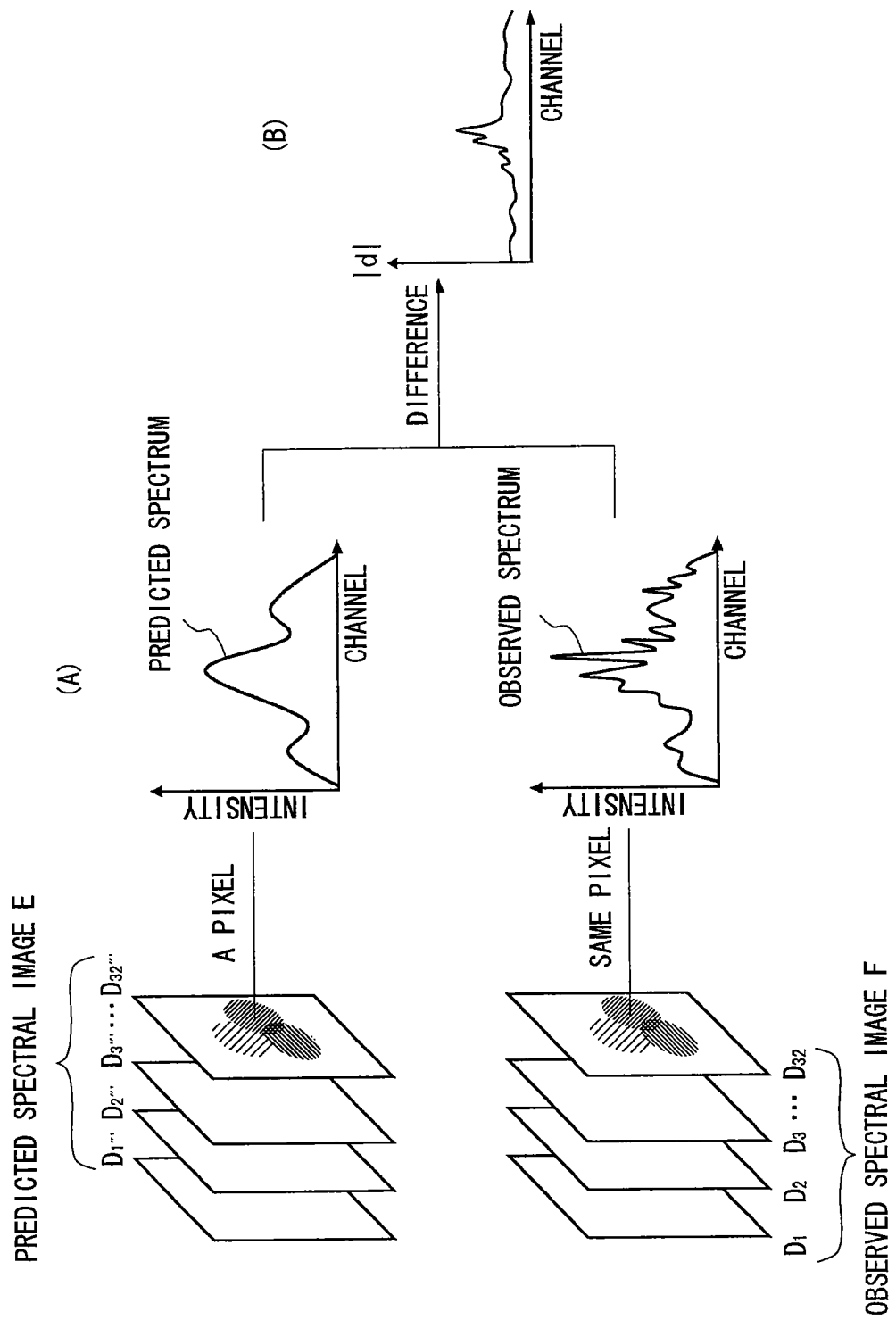

[Fig. 6]
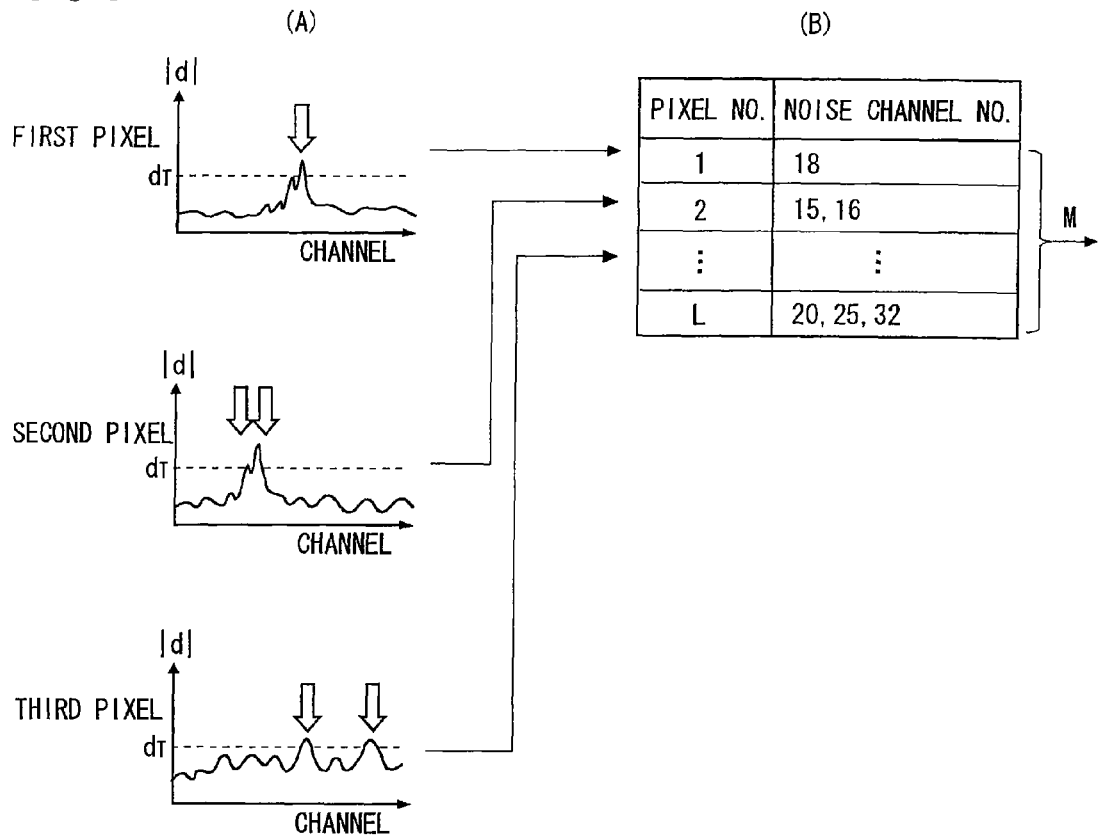
[Fig. 7]
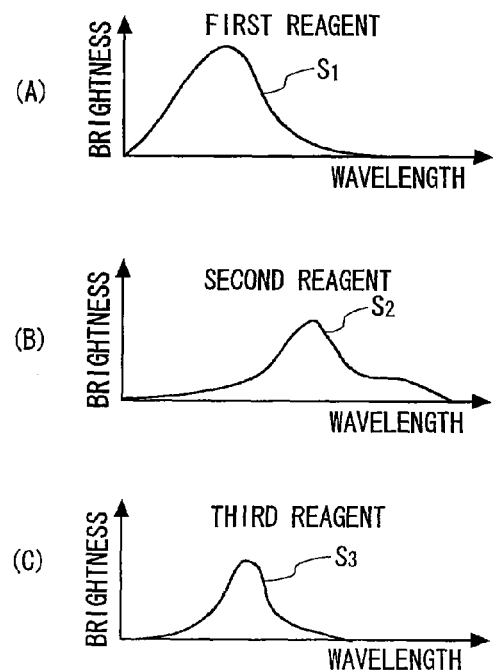

[Fig. 8]
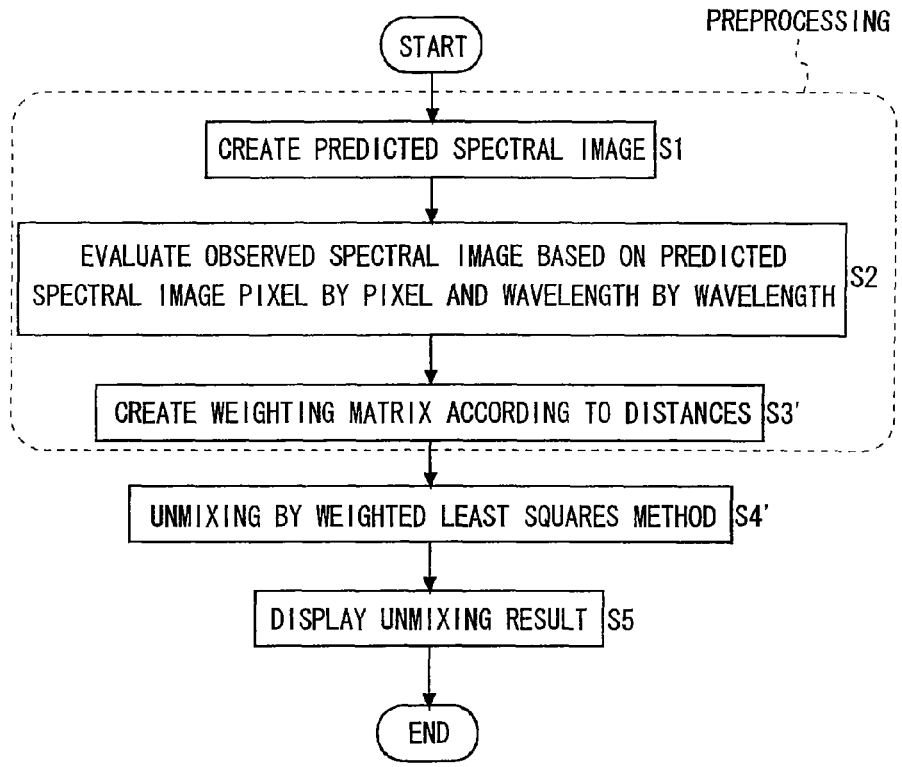
[Fig. 9]
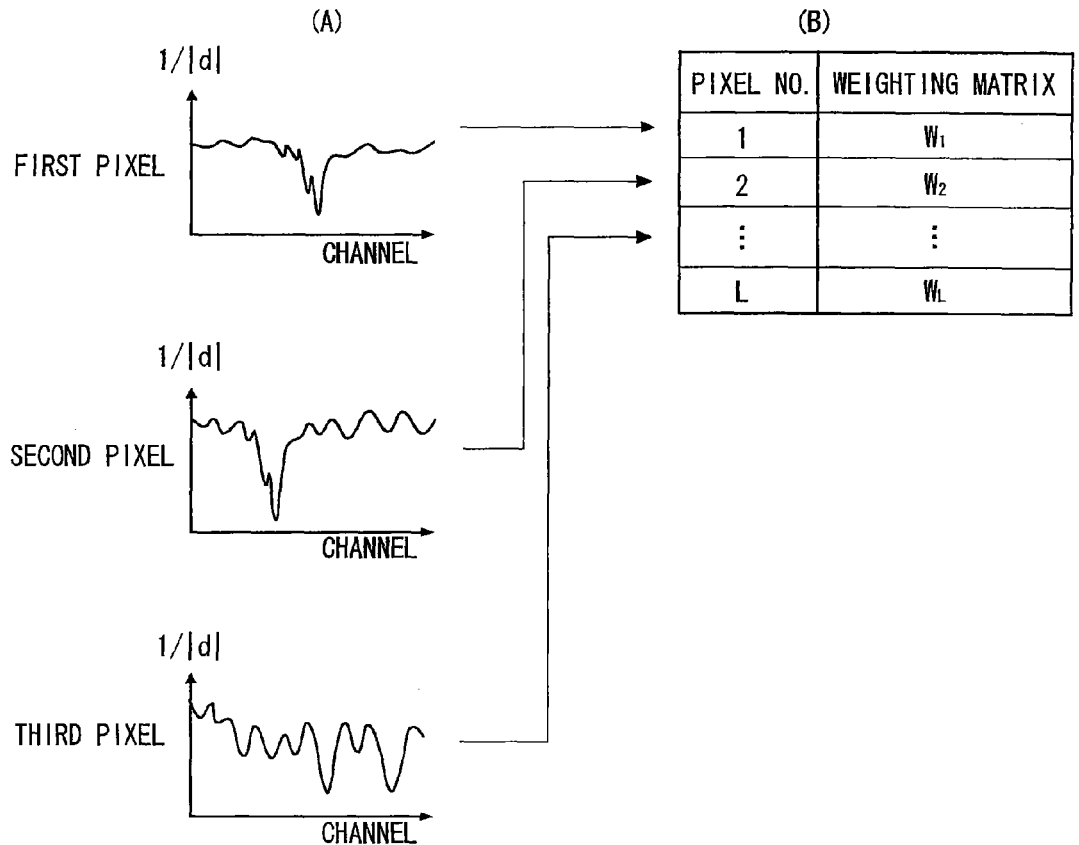

8,045,153 B2

SPECTRAL IMAGE PROCESSING METHOD, SPECTRAL IMAGE PROCESSING PROGRAM, AND SPECTRAL IMAGING SYSTEM

CROSS-REFERENCE TO RELATED APPLICATION

This application is a 371 of International Application Number PCT/JP2007/051699, filed Feb. 1, 2007, which claims the priority of Japanese Patent Application Number 2006-046509 filed Feb. 23, 2006.

TECHNICAL FIELD

The present invention relates to a spectral image processing method of processing a spectral image acquired by a microscope or the like and a computer-executable spectral image processing program. Further, the present invention relates to a spectral imaging system such as a spectral-imaging fluorescent laser microscope.

BACKGROUND ART

In dynamic observation of an organism cell, a sample is labeled by a fluorescent material such as a fluorescent reagent or a fluorescent protein and observed by an optical microscope such as a fluorescent laser microscope in some cases. When plural fluorescent materials are used simultaneously, it is necessary to detect images of respective wavelength components (a spectral image).

However, when emission wavelengths of the plural fluorescent materials overlap, the images of these respective materials cannot be separated by the optical microscope, so that an analysis method of importing the spectral image detected by the optical microscope into a computer and separating (unmixing) it into the images of the respective materials becomes effective (see Non-Patent Document 1 or the like). Incidentally, in this unmixing, emission spectral data of the respective materials disclosed by manufacturers of reagents or the like is used.

Non-Patent Document 1: Timo Zimmermann, JensRietdorf, Rainer Pepperkok, "Spectral imaging and its applications in live cell microscopy", FEBS Letters 546 (2003), P87-P92, 16 May 2003

DISCLOSURE

Problems to be Solved

However, measurement noise is superimposed on a spectral image being measured data due to instability of a light source of an optical microscope, electric noise of a light detecting element of the optical microscope, and so on, which exerts a strong influence on the accuracy of unmixing.

Hence, an object of the present invention is to provide a spectral image processing method of performing robust unmixing on measurement noise and a spectral image processing program. Further, an object of the present invention is to provide a high-performance spectral imaging system.

Means for Solving the Problems

A spectral image processing method of the present invention is a spectral image processing method of, based on an observed spectral image acquired from a specimen and emission spectral data of each of plural materials contained in the specimen, unmixing a contribution of each of the plural materials to the observed spectral image, including: an evaluating step of, based on a predicted spectral image of the observed spectral image, evaluating reliability of each component of the observed spectral image; and a reflecting step of reflecting a result of the evaluation in a content of the unmixing.

Incidentally, the predicted spectral image may be a spectral image obtained by smoothing the observed spectral image in a spatial direction.

Further, in the evaluating step, reliability of the observed spectral image may be evaluated with respect to each wavelength component.

Furthermore, in the evaluating step, reliability of the observed spectral image may be evaluated with respect to each wavelength component and each spatial component.

Moreover, in the reflecting step, a component, whose reliability is evaluated as low, of the observed spectral image may be excluded from a computation object of the unmixing.

Additionally, the unmixing may be performed by weighted least squares method of estimating the contribution after weighting error of each component of the observed spectral image, and in the reflecting step, a content of the weighting may be set according to the result of the evaluation.

Further, a spectral image processing program of the present invention causes a computer to execute any spectral image processing method of the present invention.

Furthermore, a spectral imaging system of the present invention includes: a spectral imaging unit which acquires an observed spectral image from a specimen; and a spectral image processing unit which imports the acquired spectral image and executes any spectral image processing method of the present invention.

Effect

According to the present invention, a spectral image processing method of performing robust unmixing on measurement noise and a spectral image processing program are realized. Further, in the present invention, a high-performance spectral imaging system is realized.

BRIEF DESCRIPTION OF THE DRAWINGS

FIG. 1 is a configuration diagram of a system of embodiments;

FIG. 2 is an operational flowchart of a CPU 23 of a first embodiment;

FIG. 3 is a diagram explaining step S1 (normalizing processing);

FIG. 4 is a diagram explaining step S1 (smoothing processing and denormalizing processing);

FIG. 5 is a diagram explaining step S2;

FIG. 6 is a diagram explaining step S3;

FIG. 7 is a diagram showing examples of emission spectra $S_1$, $S_2$, $S_3$ of fluorescent reagents;

FIG. 8 is an operational flowchart of the CPU 23 of a second embodiment; and

FIG. 9 is a diagram explaining step S3'.

DETAILED DESCRIPTION OF THE EMBODIMENTS

First Embodiment

A first embodiment of the present invention will be described. This embodiment is an embodiment of a spectral imaging fluorescent confocal laser microscope system.

First, the configuration of this system will be described.

FIG. 1 is a configuration diagram of this system. As shown in FIG. 1, this system includes a main body of a microscope 10, a computer 20 connected thereto, and an input device 30 and a displaying device 40 connected thereto. The input device 30 is a mouse, a keyboard, and so on, and the displaying device 40 is an LCD or the like.

In the main body 10, a laser light source 11, a dichroic mirror 12, an optical scanner 13, an objective lens 14, a sample 15, an observation lens 16, a pinhole mask 17, a spectroscopic element 18, and a multichannel-light detector 19 are placed. The sample 15 is labeled by plural types (for example, three types) of fluorescent reagents, and the multichannel-light detector 19 has many (for example, 32) wavelength channels.

The computer 20 includes a CPU 23, a ROM 24 into which a basic operation program of the CPU 23 is written, a RAM 25 used as a temporary storage means while the CPU 23 is operating, a hard disk drive 26 to save data for a long time, an interface circuit 27 interfacing the input device 30 and the displaying device 40, A/D converting circuits $21_1$, $21_2$, ..., $21_{32}$ of the same number as wavelength channels of the multichannel-light detector 19, and frame memories $22_1$, $22_2$, ..., $22_{32}$ of the same number as the A/D converting circuits. The frame memories $22_1$, $22_2$, ..., $22_{32}$, the hard disk drive 26, the CPU 23, the ROM 24, the RAM 25, and the interface circuit 27 are connected via a bus 20B. An operation program of the CPU 23 necessary for this system is previously stored in the hard disk drive 26.

Laser light (for example, having a wavelength of 488 nm) is emitted from the laser light source 11 of the main body of the microscope 10. This laser light is reflected by the dichroic mirror 12 and collected at a point on the sample 15 via the optical scanner 13 and the objective lens 14 in order. At the light collecting point, fluorescence (for example, having a wavelength of 510 nm to 550 nm) is generated, and when entering the dichroic mirror 12 via the objective lens 14 and the optical scanner 13 in order, the fluorescence is transmitted through this dichroic mirror 12 and enters the pinhole mask 17 via the observation lens 16. This pinhole mask 17 forms a conjugate relation with the sample 15 by the observation lens 16 and the objective lens 14 and has a function of letting only a necessary ray of light of the fluorescence generated on the sample 15 pass therethrough. As a result, a confocal effect of the main body of the microscope 10 can be obtained. When entering the spectroscopic element 18, the fluorescence which has passed through the pinhole mask 17 is separated into plural wavelength components. These respective wavelength components enter the wavelength channels different from each other of the multichannel-light detector 19 and detected independently and simultaneously.

The respective wavelength channels (here, 32 wavelength channels) of the multichannel-light detector 19 detect, for example, 32 kinds of wavelength components different in steps of 5 nm in a wavelength range from 510 nm to 550 nm. Respective signals outputted from the 32 wavelength channels are imported in parallel into the computer 20 and individually inputted to the frame memories $22_1$, $22_2$, ..., $22_{32}$ via the A/D converting circuits $21_1$, $21_2$, ..., $21_{32}$.

This multichannel-light detector 19 and the optical scanner 13 are synchronously driven, and thereby the signals are repeatedly outputted from the multichannel-light detector 19 during a period of two-dimensional scanning at the light collecting point on the sample 15. At this time, images of the respective wavelength channels of the sample 15 are gradually accumulated in the frame memories $22_1$, $22_2$, ..., $22_{32}$. The images (channels images $D_1$, $D_2$, ..., $D_{32}$) of the respective wavelength channels accumulated in the frame memories $22_1$, $22_2$, ..., $22_{32}$ are read in appropriate timing by the CPU 23, integrated into one spectral image F, and then stored in the hard disk drive 26.

Incidentally, in the hard disk drive 26 of the computer 20, in addition to this spectral image F, emission spectral data of the fluorescent reagents used for the sample 15 is previously stored. This emission spectral data is disclosed by manufactures of the fluorescent reagents or the like and loaded into the computer 20, for example, by the Internet, a storage medium, or the like.

Next, the operation of the CPU 23 after the spectral image F is acquired will be described.

FIG. 2 is an operational flowchart of the CPU 23. As shown in FIG. 2, after executing preprocessing constituted by creation processing of a predicted spectral image (step S1), evaluating processing (step S2), and thinning out processing (step S3), the CPU 23 executes unmixing processing (step S4), and displaying processing (step S5). These steps will be described below step by step.

Creation Processing of Predicted Spectral Image (Step S1):

In this step, first, as shown in FIG. 3(A), the CPU 23 refers to spectra of respective pixels of the spectral image F. In FIG. 3(A), spectral curves of some four pixels (a first pixel, second pixel, third pixel, fourth pixel) are shown. The horizontal axis of FIG. 3(A) is a wavelength channel, and the vertical axis thereof is a brightness value.

Then, as shown in FIG. 3(B), the CPU 23 normalizes the spectra of the respective pixels such that their brightness integral values A (the areas of regions each enclosed by the spectral curve and the horizontal axis) become one. In the normalization of each spectrum, it is only required to multiply brightness values of respective wavelength channels of the spectrum by a normalizing coefficient=(1/current brightness integral value).

Here, as shown at the right side of FIG. 3, a spectral image constituted by the spectra after the normalization is represented as F', and respective wavelength components (channel images) of the spectral image F' are represented as $D_1'$, $D_2'$, ..., $D_{32}'$.

Subsequently, as shown in FIG. 4(A), the CPU 23 performs averaging filter processing on each of the channel images $D_1'$, $D_2'$, ..., $D_{32}'$. Consequently, each of the channel images $D_1'$, $D_2'$, ..., $D_{32}'$ is smoothed in a spatial direction.

In the averaging filter processing for the channel image D', a mask (which is a computational mask), for example, having an opening of three pixels high by three pixels wide is used. This mask is put into the channel image D', and the brightness value of a target pixel located at the center of the opening of the mask is replaced with a brightness mean value of all the pixels in the opening. By repeatedly performing this processing while shifting a mask position on the channel image D', the whole channel image D' is smoothed.

Here, as shown in the lower left of FIG. 4, the respective channel images after the smoothing are represented as $D_1''$, $D_2''$, ..., $D_{32}''$ and a spectral image constituted by these channel images $D_1''$, $D_2''$, ..., $D_{32}''$ is represented as F''. In this spectral image F'', as shown in FIG. 4(B), the spectral curves of the respective pixels become smooth.

Subsequently, as shown in FIG. 4(C), the CPU 23 denomalizes spectra of the respective pixels constituting the spectral image F'' such that their brightness integral values return to the brightness integral values before the normalization (see FIG. 3(A)). In the denormalization of each spectrum, it is only required to multiply brightness values of the respective wavelength channels of the spectrum by an denormalizing coefficient=(brightness integral value before normalization/current brightness integral value).

Here, as shown in the lower right of FIG. 4, a spectral image constituted by the spectra after the denormalization is represented as a predicted spectral image E. Hereinafter, the original spectral image F is called an "observed spectral image F" in order to be distinguished from this predicted spectral image E.

Evaluating Processing (Step S2):

In this step, first, as shown in FIG. 5(A), the CPU 23 refers to a spectrum (predicted spectrum) of some pixel of the predicted spectral image E and a spectrum (observed spectrum) of the same pixel of the observed spectral image F. As shown in FIG. 5(A), between the predicted spectrum and the observed spectrum, rough shapes of both spectral curves are similar, but there is a difference in that the former is smoothed, while the latter has errors.

Hence, as shown in FIG. 5(B), the CPU 23 calculates, as evaluating values of respective wavelength channels of the observed spectrum, distances $|d_1|, |d_2|, \ldots, |d_{32}|$ between the respective wavelength channels and corresponding wavelength channels of the predicted spectrum. The distance $|d_i|$ is an absolute value of a brightness difference of an ith wavelength channel. A wavelength channel with a smaller distance $|d|$ has higher reliability, and a wavelength channel with a larger distance $|d_i|$ has lower reliability. Accordingly, hereinafter, the distance $|d|$ is called an "evaluating value $|d|$".

Further, the CPU 23 performs the above processing on the respective pixels, respectively, to calculate evaluating values $|d|$ of respective wavelength channels of each pixel and completes this step.

Thinning Out Processing (Step S3):

In FIG. 6(A), examples of the evaluating values $|d|$ of some pixels are shown. In this step, first, as shown in FIG. 6(A), the CPU 23 compares the evaluating values $|d|$ of respective wavelength channels of some pixel to a threshold value $d_T$ predetermined as shown in FIG. 6(A), finds out the one which exceeds the threshold value $d_T$ from them, and regards a wavelength channel corresponding thereto as a wavelength channel evaluated particularly low in this pixel. Hereinafter, this wavelength channel is called a "noise channel".

Further, the CPU 23 performs the above processing on all the pixels, respectively, to find noise channels of all the pixels. As a result, noise channels of the respective pixels are recognized by the CPU 23, for example, as shown in FIG. 6(B).

As shown also in FIG. 6(B), the number of noise channels is sometimes one and sometimes a plural number according to the pixels. Note, however, that if the number of noise channels of some pixel is too large, unmixing of this pixel (described later) becomes difficult, so that it is desirable that the threshold value $d_T$ in FIG. 6(A) be preset to such a value that unmixing does not become difficult by experiment or simulation.

Subsequently, the CPU 23 thins out data on the wavelength channels regarded as the noise channels from the respective pixels of the observed spectral image F. Note, however, that if the data is actually excluded from the observed spectral image F, original data on the observed spectral image F is not saved, so that here, instead of actually excluding the data, the CPU 23 creates a mask matrix M which computationally masks the data and applies it in subsequent steps. In this mask matrix M, an element corresponding to a component to be masked is zero, and an element corresponding to a component other than this is one. The CPU 23 completes this step by the creation of this mask matrix M.

Unmixing Processing (Step S4)

In this step, first, the CPU 23 reads the emission spectral data of the fluorescent reagents from the hard disk drive 26.

As shown in FIGS. 7(A), (B), (C), the emission spectral data represents emission spectra $S_1, S_2, S_3$ of three types of fluorescent reagents (a first reagent, second reagent, third reagent). These emission spectra $S_1, S_2, S_3$ are each represented by a one-dimensional matrix such as shown in equation (1).

[Equation 1]

$$S_1 = \begin{bmatrix} s_{11} \\ s_{21} \\ s_{31} \\ \vdots \\ s_{321} \end{bmatrix}, S_2 = \begin{bmatrix} s_{12} \\ s_{22} \\ s_{32} \\ \vdots \\ s_{322} \end{bmatrix}, S_3 = \begin{bmatrix} s_{13} \\ s_{23} \\ s_{33} \\ \vdots \\ s_{323} \end{bmatrix} \quad (1)$$

Note that an element $S_{ij}$ in equation (1) is a brightness value of an ith wavelength of a jth reagent. The number i of this wavelength corresponds to the number i of the wavelength channel of the observed spectral image F.

On the other hand, a spectrum f of some pixel of the observed spectral image F is represented by a one-dimensional matrix such as shown in equation (2). An element $f_i$ is a brightness value of an ith wavelength channel of this pixel.

[Equation 2]

$$f = \begin{bmatrix} f_1 \\ f_2 \\ f_3 \\ \vdots \\ f_{32} \end{bmatrix} \quad (2)$$

Accordingly, if the contribution ratio of the first reagent to this pixel is taken as $p_1$, the contribution ratio of the second reagent thereto is taken as $p_2$, and the contribution ratio of the third reagent thereto is taken as $p_3$, equation (3) holds between the spectrum f of this pixel and the contribution ratios $p_1, p_2, p_3$.

[Equation 3]

$$f = S_1 \cdot p_1 + S_2 \cdot p_2 + S_3 \cdot p_3 \quad (3)$$

Further, if the emission spectra $S_1, S_2, S_3$ are brought together and represented by one matrix S as shown in equation (4), and the contribution ratios $p_1, p_2, p_3$ are brought together and represented by one matrix P as shown in equation (5), equation (3) is transformed as shown in equation (6).

[Equation 4]

$$S = [S_1 \ S_2 \ S_3] \quad (4)$$

[Equation 5]

$$P = \begin{bmatrix} p_1 \\ p_2 \\ p_3 \end{bmatrix} \quad (5)$$

[Equation 6]

$$f = S \cdot P \quad (6)$$

Hereinafter, this matrix S is called an "emission spectrum S", and this matrix P is called a "contribution ratio P".

Hence, in unmixing of some pixel of the observed spectral image F, it is only required to assign data on the spectrum f of this pixel contained in the observed spectral image F and data on the emission spectrum S indicated by the emission spectral data to equation (6) and solve this equation for the contribution ratio P.

Note, however, that since the number of wavelength channels (here, 32) is set sufficiently larger than the number of types of fluorescent reagents (here, three) in this system, a least squares method is applied.

The least squares method is to prepare equation (7) with consideration given to an error $\epsilon$ in equation (6) and find the contribution ratio P such that a square value of the error $\epsilon$ becomes minimum.

[Equation 7]

$$f = S \cdot P + \epsilon \quad (7)$$

An equation to calculate the contribution ratio P by this least squares method is specifically shown as in equation (8).

[Equation 8]

$$P = (S^T S)^{-1} S^T f \quad (8)$$

Note that $S^T$ is a transposed matrix of S.

Accordingly, in the unmixing of some pixel of the observed spectral image F, the CPU 23 calculates the contribution ratio P by assigning the data on the spectrum f of this pixel contained in the observed spectral image F and the data on the emission spectrum S indicated by the emission spectral data to equation (8). Note, however, that at that time, the CPU 23 applies the mask matrix M (see FIG. 6(B)) and excludes a term regarding the noise channel of this pixel from equation (8). Consequently, the number of terms of equation (8) (which corresponds to the order of equation (7)) decreases, but the number of terms necessary to calculate the contribution ratio P (order of equation (7)) is secured since the above threshold value $d_T$ (see FIG. 6(A)) is set appropriately. Accordingly, the contribution ratio P to this pixel can be certainly found by the unmixing of this pixel.

Then, the CPU 23 performs the above unmixing on the respective pixels of the observed spectral image F, respectively, to calculate the contribution ratios P of the respective pixels. Thus, this step is completed.

As just described, the unmixing processing in this step is performed by the well-known least squares method, but by the application of the mask matrix M (FIG. 6(B)), components with low reliability of the observed spectral image F are not reflected at all in the computation of the unmixing processing. Accordingly, the accuracy of this unmixing processing becomes higher than that of the conventional one.

Displaying Processing (Step S5):

In this step, the CPU 23 displays the data on the contribution ratios P (contribution ratios of the respective fluorescent reagents) to the respective pixels found by the unmixing processing on the displaying device 40. The data on the contribution ratios P to the respective pixels may be displayed as numeric data, but in order to intuitively inform a user of it, it is desirable that the CPU 23 creates an unmixed image colored according to the contribution ratios P of the respective pixels and displays it.

As described above, the computer 20 of this system evaluates reliability of respective components (here, respective wavelength channel of each pixel) of the observed spectral image F and reflects a result of this evaluation in the unmixing processing, so that robust unmixing processing can be performed on measurement noise Hence, the accuracy of the unmixing processing, that is, the performance of this system is certainly improved.

Second Embodiment

A second embodiment of the present invention will be described. This embodiment is an embodiment of a spectral imaging fluorescent confocal laser microscope system. Here, only a point of difference from the first embodiment will be described. The point of difference is in the operation of the CPU 23.

FIG. 8 is an operational flowchart of the CPU 23 of this embodiment. As shown in FIG. 8, the CPU 23 of this embodiment executes creation processing of a weighting matrix (step S3') instead of the thinning out processing (step S3), and executes unmixing processing by a weighted least squares method (step S4') instead of the unmixing processing by the least squares method (step S4). These steps S3', S4' will be described below step by step.

Creation Processing of Weighting Matrix (step S3'):

At a starting point of this step, the evaluating values |d| of the respective wavelength channels of each pixel are already calculated (See FIG. 5(A)). The CPU 23 of this step refers to the evaluating values |d| regarding some pixel and creates weight values of respective wavelength channels of this pixel as shown in FIG. 9(A). The weight values of the respective wavelength channels are reciprocals of the evaluating values |d| of the respective wavelength channels. Then, the CPU 23 creates a weighting matrix W regarding this pixel by the weight values (1/|d|) of the respective wavelength channels.

If the weight value of the ith wavelength channel is taken as $1/|d_i|$, the weighting matrix W is represented by the following equation (9).

[Equation 9]

$$W = \begin{bmatrix} 1/|d_1| & 0 & \cdots & 0 \\ 0 & 1/|d_2| & & \vdots \\ \vdots & & \ddots & 0 \\ 0 & \cdots & 0 & 1/|d_{32}| \end{bmatrix} \quad (9)$$

Further, the CPU 23 performs the above processing on all the pixels, respectively, to create weighting matrixes $W_1$, $W_2, \ldots, W_L$ (L: number of pixels) of all the pixels as shown in FIG. 9(B), and completes this step.

Unmixing Processing (step S4')

In this step, the CPU 23 unmixes the respective pixels by the weighted least squares method. In the weighted least squares method, as an equation to calculate the contribution ratio P, equation (10) is used instead of equation (8).

[Equation 10]

$$P = (S^T W S)^{-1} S^T W f \quad (10)$$

Note that W is a weighting matrix of a pixel to be unmixed.

Namely, in unmixing of some pixel of the observed spectral image F, the CPU 23 calculates the contribution ratio P by assigning data on the spectrum f of this pixel contained in the observed spectral image F, data on the emission spectrum S indicated by the emission spectral data, and the weighting matrix W created regarding this pixel (see equation (9)) to equation (10).

According to this equation (10), the error of each wavelength channel (which corresponds to $\epsilon$ in equation (7)) is weighted by the weighting matrix W. Besides, according to this weighting matrix W (see equation (9)), a larger weight is given to the error of each wavelength channel whose reliability is lower.

Hence, according to this step, data on a wavelength channel, whose reliability is higher, of the pixel to be unmixed exerts a stronger influence on an unmixing result.

As just described, also in this embodiment, as in the first embodiment, the reliability of respective components (here, respective wavelength channels of each pixel) of the observed spectral image F is evaluated and a result of this evaluation is reflected in the unmixing processing, so that the accuracy of the unmixing processing, that is, the performance of this system is certainly improved.

Besides, in this embodiment, instead of excluding data on part of the observed spectral image F, a difference is provided in the degree of influence of each data, so that all data on the observed spectral image F is used to the full.

MODIFIED EXAMPLES OF RESPECTIVE EMBODIMENTS

Incidentally, in the creation processing of the predicted spectral image E of the above embodiments (step S1), the standards of the normalization and the denormalization of the spectra are set to the brightness integral value, but may be set to a brightness maximum value or a brightness intermediate value instead of the brightness integral value.

Further, in the creation processing of the predicted spectral image E of the above respective embodiments (step S1), the averaging filter processing is applied to the smoothing processing, but instead of the averaging filter processing, a different spatial filter processing such as weighted averaging filter processing or median-filter processing may be applied.

Furthermore, in the creation processing of the predicted spectral image E of the above respective embodiments (step S1), the size of the mask (size of a filter) in the smoothing processing is 3 pixels×3 pixels=9 pixels, but may be changed to a different size.

Moreover, in the creation processing of the predicted spectral image E of the above respective embodiments (step S1), the predicted spectral image E is created by three steps of (1) normalization of the spectra, (2) smoothing in the spatial directions of the spectra, (3) denormalization of the spectra, but the predicted spectral image E may be created by a different step. For example, the predicted spectral image E may be the one obtained by simply smoothing the observed spectral image F in the spatial direction.

Additionally, in the creation processing of the predicted spectral image E of the above respective embodiments (step S1), the predicted spectral image E is created based on only the observed spectral image F, but may be created based on a different spectral image. For example, by acquiring one or plural spectral images $F_t$ in different timing from the observed spectral image F and performing smoothing between the spectral images $F_t$ and the observed spectral image (namely, smoothing in a time direction), the predicted spectral image E may be created.

Further, in the above respective embodiments, the operation program of the CPU 23 is previously stored in the hard disk drive 26, but part or all of the program may be installed into the computer 20 from outside via the Internet, a storage medium, or the like.

Furthermore, in the above respective embodiments, each processing is executed by the computer 20, but part or all of the operations of the computer 20 may be executed by a device (control/image processing device) dedicated to the main body of the microscope 10.

Moreover, the main body of the microscope 10 of the above respective embodiments uses the multichannel-light detector 19 to detect respective wavelength components of incident light, but instead of the multichannel-light detector 19, a combination of one-channel light detector and a movable mask, a combination of plural one-channel light detectors and plural filters, or the like may be used. Note, however, that the use of the multichannel-light detector 19 enables both simultaneous direction of respective channels and space saving.

Further, the main body of the microscope 10 of the above respective embodiments is a fluorescent microscope which detects fluorescence generated on the sample 15, but may be a microscope which detects transmitted light or reflected light of light illuminating the sample 15. In this case, instead of the dichroic mirror 12, a beam splitter is used.

Furthermore, the main body of the microscope 10 of the above respective embodiments is a microscope (confocal microscope) which confocally detects light from the sample 15, but the function of this confocal detection may be omitted. In this case, the pinhole mask 17 becomes unnecessary.

Additionally, the main body of the microscope 10 of the above respective embodiments is a scanning microscope which optically scans the sample 15, but may be transformed into a non-scanning microscope. In this case, the optical scanner 13 becomes unnecessary.

Namely, the present invention can be applied to various devices which perform spectral imaging.

The many features and advantages of the invention are apparent from the foregoing description. It is to be understood that the invention is not limited to the described embodiments, which are intended to be illustrative and not limiting. As will readily occur to those skilled in the art, numerous changes and modifications are possible in keeping with the principles and spirit of the invention, the scope of which is defined in the appended claims.

The invention claimed is:

1. A spectral image processing method of, based on an observed spectral image acquired from a specimen and emission spectral data of each of a plurality of materials contained in the specimen, unmixing a contribution of each of said plurality of materials to said observed spectral image, comprising:
    an evaluating step of evaluating reliability of each component of said observed spectral image based on a predicted spectral image generated from said observed spectral image by processing image data of said observed spectral image;
    a reflecting step of reflecting a result of said evaluation in a content of said unmixing; and
    a displaying step of displaying a result of said unmixing.

2. The spectral image processing method according to claim 1, wherein
    said predicted spectral image is a spectral image obtained by smoothing said observed spectral image in a spatial direction.

3. The spectral image processing method according to claim 1, wherein
    in said evaluating step, reliability of said observed spectral image is evaluated with respect to each wavelength component.

4. The spectral image processing method according to claim 1, wherein
    in said evaluating step, reliability of said observed spectral image is evaluated with respect to each wavelength component and each spatial component.

5. The spectral image processing method according to claim 1, wherein
    in said reflecting step, a component, whose said reliability is evaluated as low, of said observed spectral image is excluded from a computation object of said unmixing.

6. The spectral image processing method according to claim 1, wherein
said unmixing is performed by a weighted least squares method of estimating said contribution after weighting an error of each component of said observed spectral image, and
in said reflecting step, a content of said weighting is set according to the result of said evaluation.

7. The spectral image processing method according to claim 1, wherein
the evaluating includes comparing each component of said observed spectral image with a corresponding component of said predicted spectral image.

8. The spectral image processing method according to claim 7, wherein
the components include brightness values.

9. A non-transitory computer-readable storage medium storing a spectral image processing program which causes a computer to execute a spectral image processing method in which a contribution of each of a plurality of materials of a specimen to an observed spectral image acquired from the specimen are unmixed, the spectral image processing method comprising:
an evaluating step of evaluating reliability of each component of said observed spectral image based on a predicted spectral image generated from said observed spectral image by processing image data of said observed spectral image; and
a reflecting step of reflecting a result of said evaluation in a content of said unmixing.

10. The non-transitory computer-readable storage medium according to claim 9, wherein
the evaluating includes comparing each component of said observed spectral image with a corresponding component of said predicted spectral image.

11. The non-transitory computer-readable storage medium according to claim 10, wherein
the components include brightness values.

12. A spectral imaging system, comprising:
a spectral imaging unit which acquires an observed spectral image from a specimen; and
a spectral image processing unit which imports said observed spectral image from said spectral imaging unit and performs a spectral image processing method in which contributions of each of a plurality of materials of the specimen to said observed spectral image are unmixed, the spectral image processing method comprising:
an evaluating step of evaluating reliability of each component of said observed spectral image based on a predicted spectral image generated from said observed spectral image by processing image data of said observed spectral image; and
a reflecting step of reflecting a result of said evaluation in a content of said unmixing.

13. The spectral imaging system according to claim 12, wherein
the evaluating includes comparing each component of said observed spectral image with a corresponding component of said predicted spectral image.

14. The spectral imaging system according to claim 13, wherein
the components include brightness values.

* * * * *